United States Patent [19]
Slack et al.

[11] Patent Number: 5,421,983
[45] Date of Patent: Jun. 6, 1995

[54] ANION SELECTIVE ELECTRODES CONTAINING FUMED SILICA

[75] Inventors: Lyle H. Slack; Larry E. Snyder, both of Wilmington, Del.

[73] Assignee: E. I. Du Pont de Nemours and Company, Wilmington, Del.

[21] Appl. No.: 151,098

[22] Filed: Nov. 12, 1993

[51] Int. Cl.$^6$ ............................................. G01N 27/26
[52] U.S. Cl. ..................................... 204/418; 204/403; 204/409; 204/435
[58] Field of Search ................. 204/418, 435, 409, 403

[56] References Cited

U.S. PATENT DOCUMENTS

| 3,772,175 | 11/1973 | Grubb | 204/195 |
| 4,349,426 | 9/1982 | Sugahara et al. | 204/195 |
| 4,670,127 | 6/1987 | Ritter et al. | 204/418 |
| 5,284,568 | 2/1994 | Pace et al. | 204/409 |

FOREIGN PATENT DOCUMENTS

| 55-10521 | 1/1980 | Japan . |
| 62-34044 | 2/1987 | Japan . |
| 64-50943 | 2/1989 | Japan . |

Primary Examiner—John Niebling
Assistant Examiner—Bruce F. Bell

[57] ABSTRACT

This invention relates to enhanced selectivity anion membrane electrodes useful in determining the amount of an anion of interest in a biological sample. The enhanced selectivity anion membrane formulation contains fumed silica, a polymer material, and an anion selective agent. The presence of fumed silica surprisingly minimizes or reduces the effect of interfering substances, such as salicylate which may be present in biological samples and which interfere with the determination of various anions of interest, such as chloride ($Cl^{31}$).

12 Claims, 2 Drawing Sheets

ANION SELECTIVE ELECTRODES CONTAINING FUMED SILICA

FIELD OF THE INVENTION

This invention relates to anion selective electrodes for performing potentiometric anion determinations and more particularly to anion selective electrodes having membranes containing fumed silica.

BACKGROUND OF THE INVENTION

Electrochemical measurements are widely used to determine the concentration of specific substances in fluids. These devices, referred to as ion-selective electrodes (ISEs), can be employed in a wide variety of potentiometric ion determinations, including, for example, the activity of fluoride ion in drinking water, the pH of process streams, and the determination of electrolytes in serum.

In the health care field, and particularly in the area of clinical diagnostics, ISEs are commonly used to measure the activity or concentration of various ions and metabolites present in blood plasma, serum and other biological fluids. For example, ISEs are typically used to determine $Na^+$, $Ca^{++}$, $Mg^{++}$, $K^+$, $Cl^-$, $Li^+$, pH, and carbon dioxide content in such fluids.

Conventional ion selective electrodes are typically composed of an ion selective membrane, an internal filling solution or electrolyte, and an internal reference electrode. Ion selective electrodes can be classified according to the nature of the membrane material, and include solid state membrane electrodes, glass membrane electrodes, liquid membrane electrodes having charged ion-selective agents, and neutral liquid membrane electrodes having membranes formed from an organic solution containing an electrically neutral, ion-selective agent such as an ionophore held in an inert polymer matrix. An external reference electrode used in conjunction with the ISE is typically a metal/metal halide electrode such as Ag/Ag/Cl.

An ion selective electrode exposed or subjected to a sample solution, such as a biological sample, and an external reference electrode comprise a potentiometric cell assembly. By selectively transferring the ion of interest from the sample solution to the membrane, a potential difference is generated. Under ideal selectivity conditions of the membrane for the anion of interest, the potential difference is a linear function of the logarithm of the activity ratio of the ion of interest in the two solutions contacting the membrane (Nernst equation). A semi-empirical extension of the Nernst Equation (Nikolskii Eisenmann equation) for EMF may be utilized for non-ideal conditions. By "EMF" is meant the electrical potential difference between the internal ion sensing and external reference electrode, the electrodes being electrolytically connected by means of the sample solution at zero or near zero current flow.

Conventional ISEs are typically bulky, expensive, difficult to clean and maintain, and tend to require an undesirably large volume of biological fluid. For these reasons, much attention has been directed towards developing more reliable ISEs of smaller size. These relatively small ISEs, referred to as ion-selective sensors or biosensors, can be inexpensively mass produced using techniques similar to these employed in the manufacture of electronic components, including for example, photolithography, screen printing, and ion-implantation.

Ion-selective sensors and biosensors can be manufactured at much lower production cost than conventional ISEs, making it economically feasible to offer a single-use or limited-use disposable device, thereby eliminating the difficulty of cleaning and maintaining conventional ISEs. The reduced size of ion-selective sensors further serves to reduce the required volume of patient sample. Generally, a sensor can be either a miniature version of a conventional electrode or a device constructed using one or more of the above mentioned techniques. Maximum accuracy of the analytical or diagnostic result is obtained when the sensor responds only to the concentration or activity of the component of interest and has a response independent of the presence of interfering ions and/or underlying membrane matrix effects. The desired selectivity is often achieved by an ion-selective membrane containing an ion selective agent such as an ionophore positioned over an electrical conductor.

Generally, ion-selective membranes are formed from a plasticized polymer matrix, such as polyvinyl chloride, which contains the ionophore selective for the ion of interest. For example, the ionophore valinomycin has been incorporated into a layer of membrane selective for potassium ions and trifluoroacetyl-p-butylbenzene or other trifluoroacetophenone derivatives have been used as ionophores selective for carbonate ions.

Many attempts have been made to determine chloride ion concentration in biological fluids. Both conventional electrodes and ion selective membrane electrodes as described above have been used for this purpose. These known electrodes are generally comprised of certain basic components including a solution of a polymer, such as polyvinylchloride (PVC) in a solvent such as cyclohexanone or tetrahydrofuran, an ionophore or ion selective component for selectively interacting with the chloride ion present in a sample solution, an optional plasticizing agent for rendering the membrane soft and pliable, and a reversible membrane conductor interface. Ionophores for chloride selective electrodes include various quaternary ammonium compounds, such as "Aliquat 336" (believed to be methyltricaprylcylammonium chloride) and tridodecylmethylammonium chloride (TDMAC) or quaternary phosphonium compounds. Typically, such ion selective components are chosen for their lipophilic properties and hence enhanced membrane life.

Ion selective membranes are routinely prepared by allowing the solvent present in the polymer to evaporate, thus providing for a membrane which can be molded from this mixture to a particular geometric design.

The composition of ion selective electrodes vary with respect to the amounts of polymer, plasticizer, and ionophore present in their formulations. In some electrodes, no plasticizer at all is present. U.S. Pat. No. 4,670,127 issued Jun. 2, 1987, to Ritter et al. discloses a chloride sensitive membrane having at least 50% electroactive component (ionophore) and no plasticizer at all. U.S. Pat. No. 4,349,426 issued Sep. 14, 1982 to Sugahara et al. discloses a membrane having a concentration of TDMAC from 10 to 20 percent by weight and that of PVC of from 20 to 40 percent by weight.

U.S. Pat. No. 3,772,175 issued Nov. 13, 1973, to Grubb discloses a univalent cation selective electrode prepared using a partially cured silicone rubber which is a dimethyl siloxane polymer filled with 44% by weight fumed silica filler.

A significant problem encountered in ion selective electrodes, such as chloride selective electrodes, is the presence of interfering substances present in biological samples. One such interfering substance is salicylate, which is known to interfere with chloride selective electrode determinations. Other interfering substances include bromide, ascorbate, and lipophilic anions such as rhodanide.

There is needed a simple chloride selective electrode with enhanced selectivity so as to reduce or minimize the effect of interfering substances such as other anions, lipophilic ions and other interfering substances present in biological substances.

SUMMARY OF THE INVENTION

The anion selective electrode of the present invention overcomes many of the disadvantages of known anion selective electrodes. The present invention provides for the surprising and unexpected finding that the presence of fumed silica in an anion selective electrode, such as a chloride selective electrode, reduces or minimizes interference due to the presence of various interfering substances, such as salicylate. In addition, the anion selective electrode of the present invention provide for improved membrane physical characteristics including membrane thickness, thixotropy, life, and manufacturability.

In one aspect, the invention is related to an anion-selective electrode for determining an anion in a biological sample which comprises an electrical conductor and an anion selective membrane wherein the membrane comprises:
  (a) a polymer material;
  (b) an anion-selective agent; and
  (c) from about 5% to about 50% by weight fumed silica.

Another aspect of the invention is related to a chloride selective electrode for determining chloride in a biological sample which comprises an electrical conductor and an anion selective membrane wherein the membrane comprises:
  (a) a polymer;
  (b) an anion-selective agent; and
  (c) from about 5% to about 50% by weight fumed silica.

Yet another aspect of the invention is related to a chloride selective electrode for determining chloride in a biological sample which comprises an electrical conductor and an anion selective membrane wherein the membrane comprises:
  (a) about 20% by weight carboxylated polyvinyl chloride;
  (b) about 40% by weight tridodecylmethylammonium chloride; and
  (c) about 40% by weight fumed silica.

A further aspect of the invention is related to a multi-sensor cell assembly for determining an anion of interest in a biological sample comprising:
  an electrically insulative substrate having a surface with a reference electrode and at least one ion selective electrode formed thereon, wherein one ion selective electrode has an anion selective membrane comprising a polymer material, an anion-selective agent and from about 5% to about 50% by weight fumed silica; and
  an elastomeric component positioned on the surface of the substrate defining a reference and sensor flow channel,
  the reference flow channel having means for passing reference liquids over the reference electrode,
  the sensor flow channel having means for passing sample liquids over each ion selective electrode,
  the reference and sensor flow channels defining a common outlet for removing liquids from the cell.

BRIEF DESCRIPTION OF THE FIGURES

The invention will be better understood if reference is made to the accompanying drawings, in which.

DETAILED DESCRIPTION OF THE INVENTION

Figure 1:
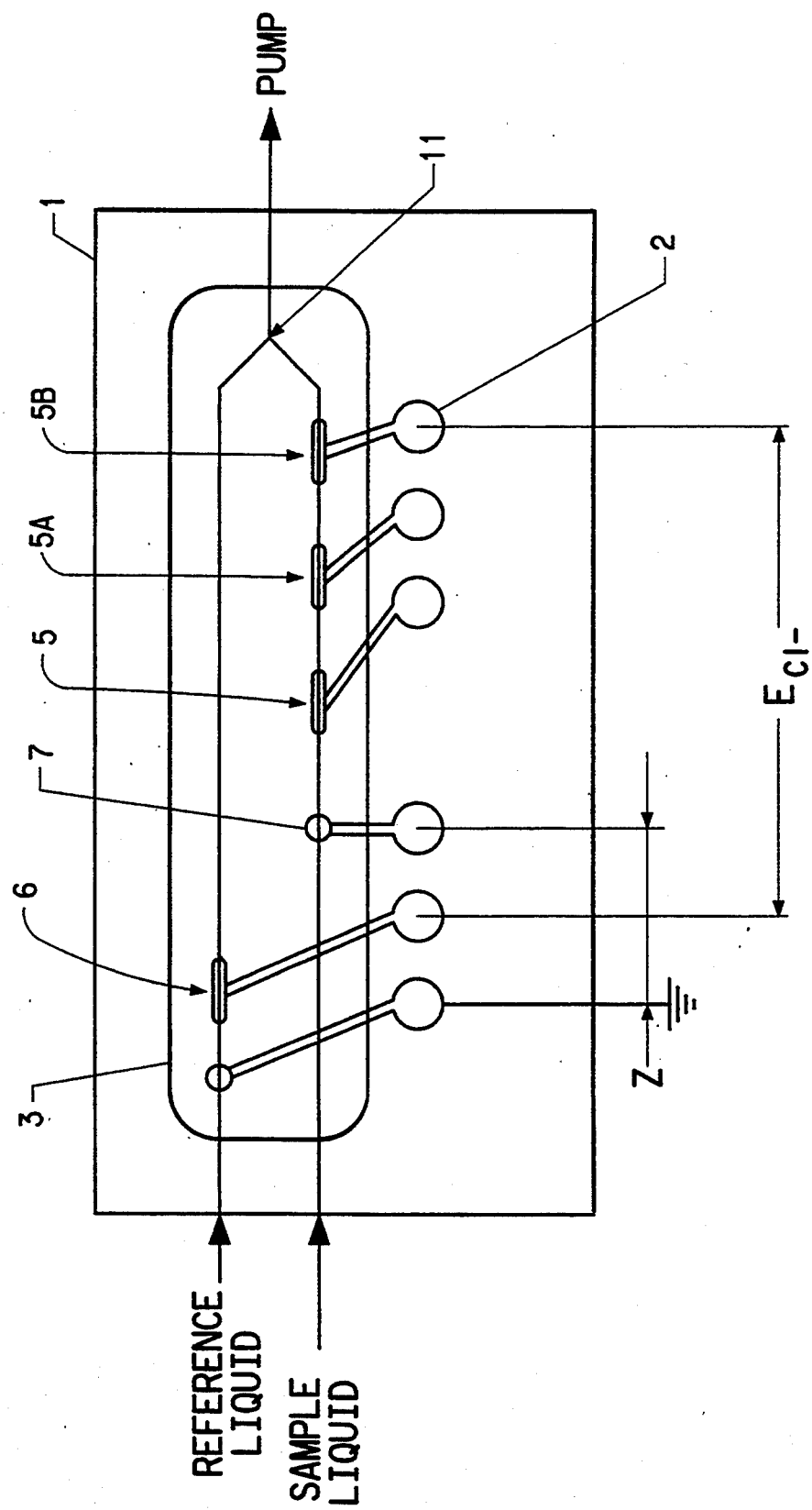
FIG. 1 is a planar view of a multisensor cell assembly having a ceramic substrate having a face with a reference electrode, a chloride ($Cl^-$) selective electrode, a sodium ($Na^+$) selective electrode, and a potassium ($K^+$) selective electrode on it.

The enhanced selectivity anion selective electrode of the present invention has a membrane which comprises a polymer material, an anion selective agent, and fumed silica. The electrode further comprises an electrically conductive material (electrical conductor) and is useful for the potentiometric determination of various anions of interest in biological samples such as blood, urine, plasma, saliva, spinal fluid, and serum.

Such samples often contain various interfering substances such as other anions and lipophilic ions which interfere with the determination of an anion of interest, i.e., the anion to be determined. Interference with the determination of chloride ion due to the presence of salicylate in biological samples can be particularly troublesome.

By "ion-selective electrode" (ISE) is meant a potentiometric electrochemical sensor, the potential of which is related to the activity or concentration of an ion of interest in a sample. Generally, the potential is linearly dependent on the logarithm of the activity of the ion of interest. The activity of an ion of interest is defined as its concentration multiplied by an activity coefficient, where the activity coefficient is generally known or available in the art.

By "anion-selective electrode" is meant an ISE where the ion of interest is an anion.

By "biological sample" is meant any fluid of biological origin including fluids which have been chemically and/or physically treated, diluted, or concentrated prior to analysis. Examples of biological samples include serum, urine, plasma, whole blood, cerebrospinal fluid, amniotic fluid, and saliva.

By "ion of interest" is meant an ion to be determined in a biological sample using an ion selective electrode.

By "anion of interest" is meant an anion to be determined in a biological sample using an anion selective electrode. Various anions of interest include but are not limited to carbonate ($CO_3^{2-}$), chloride ($Cl^-$), bromide ($Br^-$), and phosphate ($HPO_3^-$). The preferred anion selective electrode of the present invention is a chloride selective electrode for the determination of chloride ion ($Cl^-$).

A general discussion of the principles of potentiometric ion sensors is provided by Oesch et al., "Ion Selective Membranes for Clinical Use," Clinical Chemistry, Vol.32, No. 8, pp. 1448–1459, (1986).

By "polymer material" is meant any polymer suitable for use in preparing anion-selective electrodes. A variety of polymers can be utilized, including, but not limited to, polymethyl acrylate and other acrylates, silicone rubbers, polycarbonate cellulose, cellulose ester, poly(vinyl acetate), polyurethane, poly(vinyl butyral), polyvinyl chloride, carboxylated polyvinyl chloride, and other copolymers of vinyl chloride. By cellulose ester is meant all ester derivatives of cellulose, including, but not limited to, cellulose acetate, cellulose butyrate, and other members of a homologous series. By poly(vinyl butyral) is meant a copolymer of vinyl butyral, vinyl alcohol, and vinyl acetate. Carboxylated polyvinyl chloride is preferred.

The amount of polymer material used is that amount sufficient to produce a membrane of suitable thickness and structural integrity for use as an anion selective electrode. The preferred amount of polymer material utilized in the anion-selective electrode of the present invention is about 20% by weight. The thickness of the anion selective membrane of the present invention can vary from about $1\mu$ to about $1000\mu$ in thickness and is preferably about $20\mu$ in thickness.

By "anion-selective agent" is meant any substance which provides for selective interaction with the anion of interest, i.e., the anion to be determined in the sample. Examples of such anion-selective agents include quaternary ammonium compounds (chlorides) and quaternary phosphonium chlorides. Examples of particular anion-selective agents for use in the determination of chloride ion are "Aliquat 336", believed to be methyltricaprylcyl ammonium chloride and tridodecylmethylammonium chloride (TDMAC). The preferred chloride selective agent for use in the chloride selective electrode of the present invention is TDMAC.

The amount of anion-selective agent used is that amount sufficient to provide for maximum selectivity of the membrane without altering or destroying the structural integrity of the membrane. The amount of anion-selective agent can vary from about 0.01% by weight to about 65% by weight. A concentration of about 40% by weight anion-selective agent is preferred.

By "fumed silica" is meant silica ($SiO_2$) particles having a size range of from about 5 nm to about 100 nm. Such fumed silica particles may have been subjected to various chemical treatments which alter the hydrophobicity or hydrophilicity characteristics of the particles. Hydrophobic fumed silica particles are preferred. A suitable source of fumed silica is commercially available under the tradename Aerosil® as Aerosil R972, from the DeGussa Corp., New Jersey, U.S. Aerosil R972 particles have been rendered hydrophobic by the reaction of some of the silanol groups of the particles with dimethyldichlorosilane. The amount of fumed silica contained in the anion selective electrode of the present invention can vary from about 5% by weight to about 50% by weight; 40% by weight is preferred.

The anion selective membrane of the anion selective electrode of the present invention can be prepared by mixing a suitable amount of polymer material dissolved in an appropriate solvent with a suitable amount of anion-selective agent to produce an anion selective polymer material. The solvent used can be any solvent commonly used to prepare conventional membranes and can include, for example, isophorone, dimethyl adipate, and cyclohexanone. A suitable amount of fumed silica can then be added to the anion selective polymer material using any of a variety of means, provided that the fumed silica is thoroughly dispersed in the anion selective polymer material. The fumed silica can be added to the anion-selective polymer material using, for example, a muller or high shear mixer. Various commercially available mullers can be used to achieve this purpose such as the Hoover Automatic Muller Model M5 (New Jersey, U.S.). When using the Hoover Automatic Muller Model M5 three cycles of 20 revolutions each is suitable.

Any order of mixing for the polymer material, anion selective agent, and fumed silica can be used in preparing the anion selective membrane of the present invention. The resulting fumed silica containing anion selective polymer material can then be used to prepare anion selective membranes which, in turn, can be used to prepare enhanced selectivity anion selective electrodes. The production of such electrodes can be achieved using known techniques and methodology. The enhanced anion selective electrode 5b depicted in FIGS. 1 and 2 is preferred.

Enhanced selectivity anion selective electrodes of the present invention can be utilized with other ISEs in multisensor assemblies.

Figure 2:
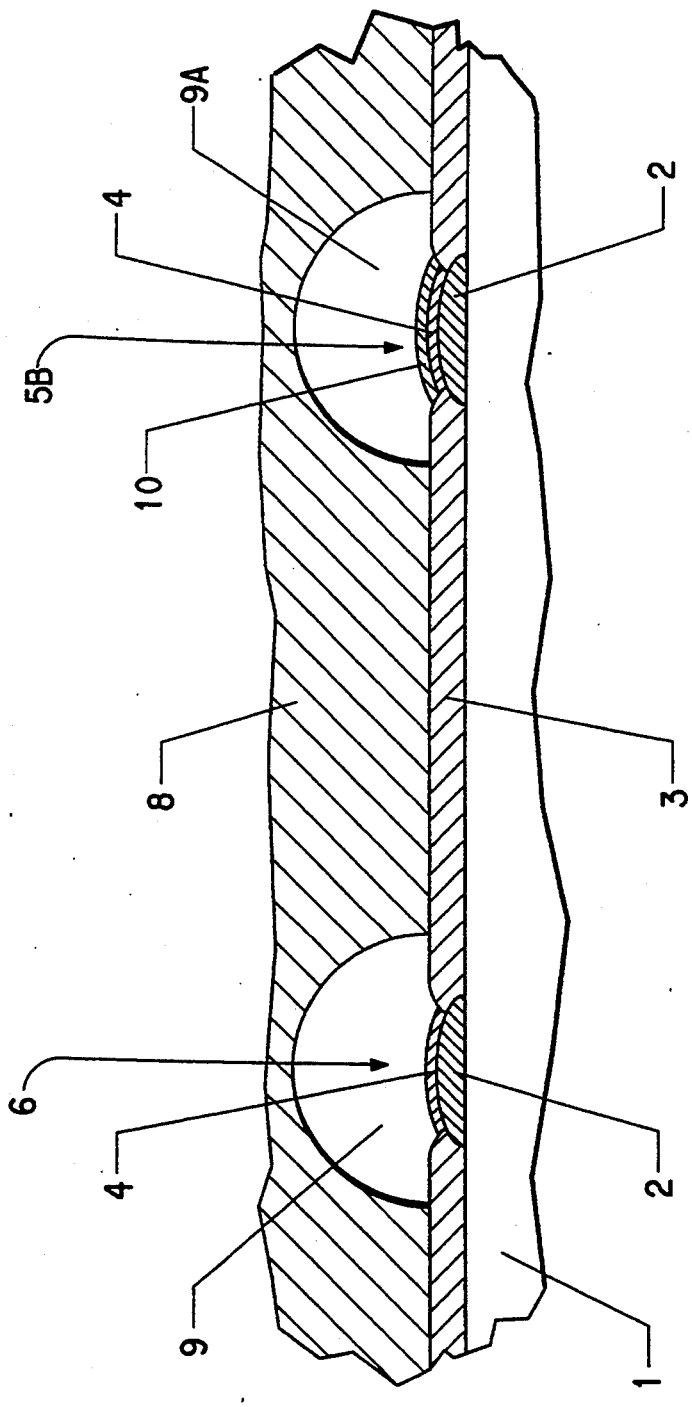
FIG. 2 is a fragmentary cross-sectional view of the multi-sensor cell assembly of FIG. 1.

For example, FIGS. 1 and 2 depict a multisensor flow cell having an enhanced selectivity anion selective electrode. The enhanced selectivity anion selective electrode is formed on an electrically insulative ceramic substrate 1 which is available commercially and can, for example, be purchased from the Coors Ceramics Co. The ceramic substrate 1 has a surface which has been appropriately screen printed with a suitable electrically conductive material (electrical conductor 2) to provide for appropriate electrical contacts for each ion selective electrode 5, 5A, 5B, and a reference electrode 6. Ion selective electrode 5b is an enhanced selectivity chloride selective ion selective electrode of the present invention having a membrane containing fumed silica, sensor electrodes 5A and 5 are potassium and sodium ion selective membrane electrodes, respectively. The electrical conductor 2 can be formed from a silver paste, also available commercially as, for example, silver paste QS175 (E. I. du Pont de Nemours and Company, Delaware, U.S.). A dielectric layer 3 serves to electrically isolate the electrical conductor 2 and to provide a well for the electrical conductor 2 and the chloride selective membrane 10. A layer composed of a mixture of silver and silver chloride (Ag/AgCl) 4 is screen printed on the electrical conductor 2 for the ion selective electrode 5b and the reference electrode 6. A fumed silica-containing chloride selective polymer material prepared, as described above, is positioned onto the silver/silver chloride layer 4 to form the chloride selective membrane 10. The multisensor assembly can be appropriately fired using known thick film belt techniques after each layer is added.

An elastomeric component 8 contacts with the surface of the ceramic substrate 1 to define a reference flow channel 9 and a sensor flow channel 9A. The reference flow channel 9 and sensor flow channel 9A define means for passing reference liquids and sample liquids over the reference 6 and ion selective electrodes 5, 5A and 5B, respectively. Furthermore, the reference flow channel 9 and sensor flow channel 9A define a common outlet 11, for removing liquids from the cell.

The elastomeric component 8 of the multisensor cell assembly of the present invention can be of any form suitable for defining flow channels 9 and 9A. For example, the multisensor cell assembly of the present invention can be used in conjunction with the disposable sensor assembly or cartridge disclosed in copending application Ser. No. 07/916,231.

The preferred anion selective electrode of the present invention is a chloride selective electrode. The preferred chloride selective membrane contains about 40% by weight fumed silica, about 40% by weight TDMAC as a chloride-selective agent, and about 20% by weight carboxylated polyvinyl chloride.

EXAMPLE

A. Preparation of A Chloride Ion Selective Membrane

Into a 400 milliliter (ml) beaker containing 88 grams (g) of the solvent isophorone (Fluka Chemical Co., New York, U.S.A.) was added 12 g of carboxylated polyvinyl chloride (CPVC) (Aldrich Chemical Co., Wisconsin, U.S.A.). The resulting suspension was covered to prevent evaporation of the solvent and heated using a hot plate/stirrer over a period of about 15 to 20 minutes to a temperature of about 60° C. When the suspension becomes transparent, the heat was turned off and stirring was continued for an additional 5 minutes. The resulting polymer material was transferred to a sealed container for subsequent use in preparing a chloride selective membrane.

Into a 1 ounce container containing 0.98 g TDMAC (Aldrich Chemical Co., Wisconsin, U.S.A.) was added 4.08 g of the polymer material prepared as described above. The container was sealed and heated at 50° C. for 30 minutes to dissolve the TDMAC. The resulting mixture was stirred and an amount of 0.765 g fumed silica ($SiO_2$) (available from Degussa Co., as Aerosil R972, Ohio, U.S.A.) was dispersed or mulled into the mixture using a muller (Hoover Automatic Muller Model M5, New Jersey, U.S.) using three cycles of 20 revolutions each. An amount of 0.176 g silane (Aldrich Chemical Co., catalogue no. 23,578-4,, Wisconsin, U.S.) was then added to the mixture with stirring. The resulting chloride selective polymer material was subsequently utilized in preparing a chloride selective electrode.

B. Preparation of Chloride Ion Selective Electrode

The chloride selective polymer material prepared as described above in A was incorporated into the multisensor flow assembly of FIG. 1 as a chloride selective electrode as follows.

The multisensor flow assembly, illustrated in FIG. 1 was prepared as follows. Ceramic substrates (Coors Ceramics Co., U.S.) were ultrasonically cleaned and dried. A silver pattern serving as a conductor 2 was screen printed onto the ceramic substrate using silver paste QS175 (E. I. du Pont de Nemours and Company, Delaware, U.S.). The ceramic substrates were then fired in a thick film belt furnace such as that commonly used in thick film technology, employing a heating rate of 95° C. per minute to 850° C., at 850° C. the ceramic substrates were held for ten (10) minutes and then cooled at a rate of 95° C. per minute. Three layers of thick film dielectric QS482 (E. I. du Pont de Nemours and Company, Delaware, U.S.) were then screen printed onto the ceramic substrate and dried. The ceramic substrate containing the three dielectric layers was then fired in the thick film belt furnace by employing a heating rate of 95° C. per minute to 850° C., at 850° C. the ceramic substrates were held for ten (10) minutes and then cooled at a rate of 95° C. per minute.

A mixture of silver and silver chloride (80% silver and 20% silver chloride by weight) was then screen printed as layer 4 on the electrical conductor 2 as shown in FIG. 2. The ceramic substrate was then fired by heating at 100° C. per minute to 600° C., holding at 600° C. for ten minutes and cooling at 100° C. per minute. The resulting finished ceramic substrate was then stored in nitrogen until used as follows.

The chloride selective polymer material prepared as described above in Part A above was dispensed onto the ceramic substrate using a syringe to form the chloride selective membrane 10 of the chloride selective electrode 5b depicted in the multisensor flow assembly shown in FIGS. 1 and 2. The dispensed chloride selective polymer material was then cured by heating the ceramic substrate at 80° C. for 90 minutes to form the chloride selective membrane. The resulting ceramic substrate assembly was then exposed to an ultraviolet source at an intensity of 750 millijoules per square centimeter. The cured ceramic substrate assembly was then mounted in a cartridge having an elastomer component 8, FIG. 2, which is pressed against the finished ceramic substrate so as to define reference and sensor flow channels 9 and 9A respectively (FIG. 2) thus providing means for reference and sample liquids to flow over the reference 6 and ion selective electrodes 5, 5A, 5B. An air detect 7 for the multisensor flow assembly provides a means for detecting interfering air bubbles which may be present in the reference and/or sample liquids.

The sodium selective electrode 5 and potassium selective electrode 5a were similarly prepared by dispensing sodium and potassium selective polymer materials onto the finished ceramic substrate.

C. Assay for Chloride Using Chloride Selective Electrode

Chloride ion selective electrodes were prepared using the procedure described above (but with varying amounts of silica, TDMAC, and CPVC as shown in Table 1 below) and tested for their selectivity to chloride ion. The membrane compositions prepared were as follows:

TABLE 1

| Membrane | % Silica (by weight) | % TDMAC (by weight) | % CPVC (by weight) |
|---|---|---|---|
| 1 | 0 | 60 | 40 |
| 2 | 10 | 54 | 36 |
| 3–9 | 40 | 40 | 20 |

The ion selective electrode in which the membrane formulation did not contain silica was prepared using exactly the same procedure as was used in preparing the ion selective electrode with the fumed silica containing membrane formulation with the exception that the mulling step which provided for the addition of the fumed silica was omitted in preparation of the ion selective electrode in which the membrane formulation did not contain silica.

The multisensor cell assembly of FIG. 1 was used to compare the enhanced selectivity chloride selective membrane electrode of the present invention with chloride selective electrodes having known membrane formulations. The voltage which changes with varying $Cl^-$ concentrations is located at the junction between the sample solution or liquid and the ion selective membrane. The voltage, E, is given by the Nernst equation and results from a space charge layer of $Cl^-$ ions temporarily attracted to the ion selective agent TDMAC present in the chloride selective electrode.

The chloride selective electrode prepared as described above was calibrated using standard solutions containing known concentrations of chloride ions, two standard solutions were used contained 112 and 50 millimols per liter (mmol/lit) and were chosen so as bracket the concentrations of chloride ions likely to be encountered in test samples. The calibration was done by exposing the Cl⁻electrode first to one standard solution and then to the other. A Cl⁻concentration versus voltage calibration curve was constructed and the test samples described below were tested for Cl⁻concentrations. The Cl⁻concentration for the test sample solutions were interpolated from the calibration curve.

Four test solutions were prepared as shown below in Table 2:

TABLE 2

| Test Solution No. | Chloride (Cl⁻) (mmol/L) | Sodium (Na⁺) (mmol/L) | Potassium (K⁺) (mmol/L) | Salicylate (mmol/L) | Carbonate CO₃⁻⁻ (mmol/L) |
|---|---|---|---|---|---|
| 1 | 124 | 175 | 9.1 | 0 | 58.9 |
| 2 | 124 | 175 | 9.1 | 3.22 | 58.9 |
| 3 | 100 | 137.5 | 4.55 | 0 | 28.05 |
| 4 | 101 | 142.0 | 4.55 | 3.0 | 28.65 |

Membrane electrode 1 was tested with Test Solution Nos. 1 and 2 and membrane electrodes 2-9 were tested with Test Solution Nos. 3 and 4 and the amount of chloride determined. The results are shown in Table 3 below.

TABLE 3

| Membrane Electrode | Chloride (mM) (Test Solution No. 1 with no salicylate)** | Chloride (mM) (Test Solution No. 2 with salicylate) | Error*** (mM) Chloride |
|---|---|---|---|
| 1 (no silica) | 120.03 | 139.14 | 19.11 |
| 2 (10% silica) | 102.61 | 114.44 | 11.84 |

| Membrane Electrode 3-9 40% silica) | Chloride (mM) (Test Solution No. 3 with no salicylate)** | Chloride (mM) (Test Solution No. 4 with salicylate) | Error*** (mM) Chloride |
|---|---|---|---|
| 3 | 97.27 | 104.07 | 5.80 |
| 4* | 101.77 | 104.24 | 1.47 |
| 5* | 101.83 | 103.44 | 0.61 |
| 6* | 101.66 | 103.00 | 0.34 |
| 7* | 101.25 | 102.14 | −0.11 |
| 8* | 102.58 | 103.69 | 0.11 |
| 9* | 101.72 | 103.38 | 0.66 |

*membranes 4-9 were subjected to about 4 hours prior usage and were produced approximately 7 days prior to testing
**Test Solution No. 1 contained 100 mM chloride for membrane electrodes 1-3 and 101 mM chloride for membrane electrodes 4-9
***the error attributed to salicylate interference = (Test Solution No. 2 - 101.00) − (Test Solution No. 1 - 100.00)

The results shown in Table 1 indicate a significant reduction in interference from salicylate when using the enhanced selectivity chloride selective electrode containing fumed silica.

What is claimed is:

1. An anion-selective membrane electrode for determining an anion in a biological sample which comprises an electrical conductor and an anion selective membrane wherein the membrane comprises:
   (a) a polymer material;
   (b) an anion-selective agent; and
   (c) from about 5% to about 50% by weight fumed silica.

2. The anion-selective membrane electrode of claim 1 wherein the polymer material is selected from the group consisting of polymethyl acrylate and other acrylates, silicone rubbers, polycarbonate cellulose, cellulose ester, poly(vinyl acetate), polyurethane and other urethanes, poly(vinyl butyral), polyvinyl chloride, carboxylated polyvinyl chloride, and other copolymers of vinyl chloride.

3. A chloride selective membrane electrode for determining chloride in a biological sample which comprises an electrical conductor and an anion selective membrane wherein the membrane comprises:
   (a) a polymer;
   (b) an anion-selective agent; and
   (c) from about 5% to about 50% by weight fumed silica.

4. The chloride selective membrane electrode of claim 3 wherein the polymer material is selected from the group consisting of polymethyl acrylate and other acrylates, silicone rubbers, polycarbonate cellulose, cellulose ester, poly(vinyl acetate), polyurethane and other urethanes, poly(vinyl butyral), polyvinyl chloride, carboxylated polyvinyl chloride, and other copolymers of vinyl chloride.

5. The chloride selective membrane electrode of claim 3 wherein the chloride selective agent is selected from the group consisting of tridodecylmethylammonium chloride and Aliquat 336.

6. A chloride selective membrane electrode for determining chloride in a biological sample which comprises an electrical conductor and an anion selective membrane wherein the membrane comprises:
   (a) about 20% by weight carboxylated polyvinyl chloride;
   (b) about 40% by weight tridodecylmethylammonium chloride; and
   (c) about 40% by weight fumed silica.

7. The anion selective membrane electrode of claims 1, 3, or 6 wherein the electrical conductor is positioned on a surface of an electrically insulative substrate.

8. The anion selective membrane electrode of claim 7 wherein the substrate is ceramic.

9. The multisensor cell assembly of claim 8 wherein the substrate is ceramic.

10. The multisensor cell assembly of claim 9 wherein the three ion selective electrodes are a potassium selective electrode, a sodium selective electrode, and a chloride selective electrode.

11. The multisensor cell assembly of claim 8 wherein there are three ion selective electrodes.

12. A multisensor cell assembly for determining an anion of interest in a biological sample comprising:
   an electrically insulative substrate having a surface with a reference electrode and at least one ion selective electrode formed thereon, wherein one ion selective electrode has an anion selective membrane comprising a polymer material, an anion-selective agent, and from about 5% to about 50% by weight fumed silica; and
   an elastomeric component positioned on the surface of the substrate defining a reference and sensor flow channel,
   the reference flow channel having means for passing reference liquids over the reference electrode,
   the sensor flow channel having means for passing sample liquids over each ion selective electrode,
   the reference and sensor flow channels defining a common outlet for removing liquids from the cell.

* * * * *